(12) United States Patent  
Kashiwamura et al.

(10) Patent No.: US 6,770,772 B2
(45) Date of Patent: Aug. 3, 2004

(54) TRANSITION METAL COMPOUND, POLYMERIZATION CATALYSTS FOR OLEFIN, OLEFIN POLYMERS AND PROCESS FOR THEIR PRODUCTION

(75) Inventors: Takashi Kashiwamura, Chiba (JP); Takuji Okamoto, Chiba (JP); Yutaka Minami, Chiba (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/129,099

(22) PCT Filed: Sep. 21, 2001

(86) PCT No.: PCT/JP01/08238

§ 371 (c)(1),
(2), (4) Date: May 10, 2002

(87) PCT Pub. No.: WO02/24714

PCT Pub. Date: Mar. 28, 2002

(65) Prior Publication Data

US 2003/0017940 A1 Jan. 23, 2003

(30) Foreign Application Priority Data

Sep. 21, 2000 (JP) ........................................ 2000-286539

(51) Int. Cl.⁷ ............................................... C07F 17/00
(52) U.S. Cl. ........................... 556/53; 556/51; 502/103; 502/118; 526/160; 526/170; 526/943; 526/351
(58) Field of Search ....................... 556/51, 53; 502/103, 502/117; 526/160, 170, 943

(56) References Cited

U.S. PATENT DOCUMENTS 5,854,165 A * 12/1998 Yabunouchi et al. ....... 502/117
6,339,135 B1 * 1/2002 Kashiwamura et al. ..... 526/160

FOREIGN PATENT DOCUMENTS

JP  2000-95808  4/2000
JP  2001-64314  3/2001

* cited by examiner

*Primary Examiner*—David W. Wu
*Assistant Examiner*—Rip A. Lee
(74) *Attorney, Agent, or Firm*—Oblon, Spivak, McClelland, Maier & Neustadt, P.C.

(57) ABSTRACT

The present invention relates to a transition metal compound represented by the general formula (I), and a olefin polymerization catalyst comprising above transition metal compound and activating co-catalyst as the main components.

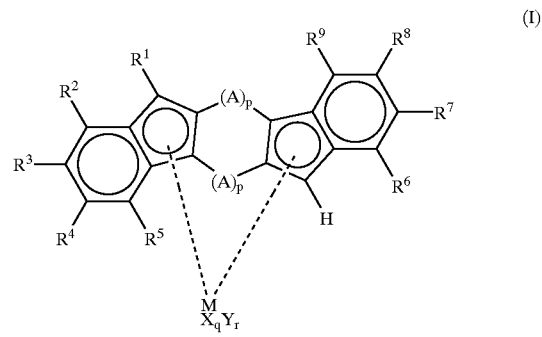

(wherein, M represents a metal element in the groups 3 to 10 of the periodic table or in the lanthanoide series, X represents a σ bonding ligand bonded to M, Y represents a Lewis base, A represents a cross-linking group, p is an integer of 1 to 20, q is an integer of 1 to 5 and represents [(valence of M)−2], r is an integer of 0 to 3. $R^1$ represents a group in above $R^2$ to $R^9$ except hydrogen atom). The present invention provides a transition metal compound useful for olefin polymerization catalyst, and olefin polymerization catalyst using above compound.

19 Claims, No Drawings

TRANSITION METAL COMPOUND, POLYMERIZATION CATALYSTS FOR OLEFIN, OLEFIN POLYMERS AND PROCESS FOR THEIR PRODUCTION

FIELD OF THE INVENTION

The present invention relates to a transition metal compound, an olefin polymerization catalyst, the olefin polymer obtained by using the said catalyst, and its production method. More specifically, the present invention relates to a transition metal compound which is highly efficient for production, useful and novel double cross-linked metallocene complex, the olefin polymerization catalyst containing above transition metal compound for efficiently providing a homogeneous, highly stereoregular olefin homopolymer or copolymer having narrow molecular weight distribution, above described olefin based polymer and its production method.

BACKGROUND ARTS

Heretofore, a combination of transition metal compound and aluminoxane is known as highly active and soluble type olefin polymerization catalyst [Japanese Patent Application Laid-Open S58-19309 (1983), Japanese Patent Application Laid-Open S60-217209 (1985)]. It was also reported that cationic ingredient was useful as an active ingredient for soluble type olefin polymerization catalyst [Journal of the American Chemical Society (J. Am. Chem. Soc.) Vol.81, p.81 (1959), Vol.82, p. 1953 (1960), Vol.107, p.7219 (1985)]. Examples of isolating this active ingredient for application of olefin polymerization were described in Journal of the American Chemical Society (J. Am. Chem. Soc.) Vol.108, p. 7410 (1986), Japanese Patent Application Laid-Open H1-502636, H3-139504, European Patent Laid-Open 468651, and examples of using this active ingredient together with organic aluminum compound were described in Japanese Patent Application Laid-Open H3-207704 (1991), International Patent Laid-Open 92-1723.

However, those catalysts were not quite satisfactory with respect to the catalyst activity for olefin polymerization, copolymerization characteristics or homogeneity of polymer composition and molecular weight distribution. On the other hand, the catalyst for providing isotactic polypropylene has $C_2$ axis of symmetry such as $Me_2$ Si $(2,3,5\text{-}Me_3C_5H)(2',4',5'\text{-}Me_3C_5H)$ $ZrCl_2$ in the molecule, structurally having two stereoisomers of racemi form and meso form, and it was necessary to separate racemic form to completely remove meso form to obtain a homogeneous isotactic polypropylene having narrow molecular weight distribution. This resulted in a high cost of production.

On the other hand, as single cross-linked metallocene complex is thermally weak and tends to change property of active site due to heat of polymerization, multi cross-linked type (double cross-linked type) metallocene complex is under study. However, only a few examples of synthesis of multi cross-linked type metallocene complex were reported such as in the International Patent Laid-Open 93-20113, and Organometallics Vol.12, p.1931 (1993), Organometallics Vol.13, p.3868 (1994), Organometallics Vol.17, p.5528 (1998). Although its behavior as polymerization catalyst was reported in Organometallics Vol.12, p.5528 (1998), separation of meso form and racemic form of the metallocene complex was necessary for obtaining isotactic polypropylene, and the obtained molecular weight of the polypropylene was low.

Catalysts for production of polypropylene using multi cross-linked metallocene complex were also disclosed in the International Patent Laid-Open 99-67303, and the Japanese Patent Application Laid-Open 2000-256411, solving above problems. However, melting point of the obtained polymer is low, and no polymer having a good balance between molecular weight and stereoregularity was obtained.

All the references cited above are related to symmetrical metallocene complex having two ring-structured ligands of the same structure coordinated around the center metal. For example, in the above described International Patent Laid-Open 99-67303, as well as in the Japanese Patent Application Laid-Open 2000-256411, double cross-linked metallocene complex having two indenyl rings with substituting group in the tertiary position was disclosed, but the yield of the ligand was low.

DISCLOSURE OF THE INVENTION

With such background as described above, the object of the present invention is to provide a transition metal compound which is highly efficient for production and useful novel double cross-linked metallocene complex, a highly active polymerization catalyst for giving a high molecular weight and homogeneous olefin based polymer with narrow molecular weight distribution, and an olefin based homopolymer or copolymer having high molecular weight, homogeneous composition, narrow molecular weight dictribution, high stereoregularity and high melting point, prepared by using above catalyst.

The inventors of the present invention, as the result of their intensive study for achieving above described object, have found that a transition metal compound of a novel asymmetrical type double cross-linked metallocene complex with a specified structure was useful as a component of olefin polymerization catalyst, and that the polymerization catalyst comprising above transition metal compound and an activating co-catalyst has high activity, and efficiently provide olefin based polymer and copolymer with high molecular weight, homogeneous composition and narrow molecular weight distribution. The present invention has been completed based on such findings.

Namely, the present invention provides (1) a transition metal compound represented by the general formula (I),

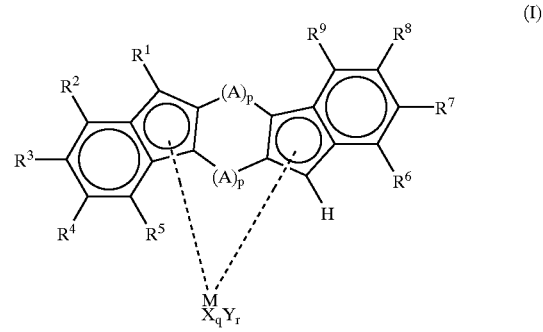

[wherein, M represents a metal element in the groups 3 to 10 group of the periodic table or in the lanthanide series, X represents a σ bonding ligand bonded to M, if X is plural, X may be the same or different, or cross-linked with indenyl ring or Y.

Y represents a Lewis base, if Y is plural, Y may be the same or different, or may be cross-linked with indenyl ring or X. A represents a cross-linking group, p is an integer of 1 to 20, q is an integer of 1 to 5 and represents [(valence of M)−2], r is an integer of 0 to 3. $R^1$ represents a halogen atom, a hydrocarbon group having 1 to 20 carbon atoms, a halogen containing hydrocarbon group having 1 to 20 carbon atoms, a silicon containing group or a hetero-atom containing group. Each of $R^2$ to $R^9$ represents respectively hydrogen atom, a halogen atom, a hydrocarbon group having 1 to 20 carbon atoms, a halogen containing hydrocarbon group having 1 to 20 carbon atoms, a silicon containing group or a hetero-atom containing group, they may be the same or different with each other, or may form a ring with neighboring group.]

(2) (A) Olefin polymerization catalyst comprising a transition metal compound represented by above general formula (I) and an activating co-catalyst as the main components, (3) Olefin based polymer obtained by using above olefin polymerization catalyst, and (4) Production method of above olefin based polymer characterized by homo polymerizing olefins, or co-polymerizing other olefins and/or other monomer, under the presence of above olefin polymerization catalyst.

PREFERRED EMBODIMENTS OF THE INVENTION

Transition metal compound of the present invention is a novel double cross-linked type metallocene complex represented by the general formula (I).

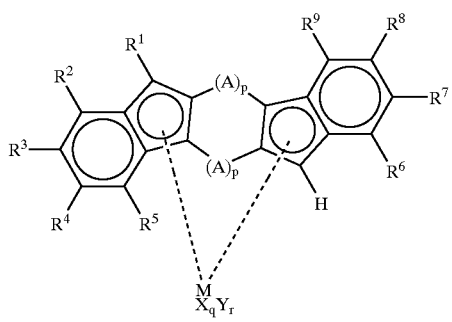

(I)

In the general formula (I), $R^1$ represents a halogen atom, a hydrocarbon group having 1 to 20 carbon atoms, a halogen containing hydrocarbon group having 1 to 20 carbon atoms, a silicon containing group or a hetero-atom containing group; $R^2$ to $R^9$ represents hydrogen atom, a halogen atom, a hydrocarbon group having 1 to 20 carbon atoms, a halogen containing hydrocarbon group having 1 to 20 carbon atoms, a silicon containing group or a hetero-atom containing group. $R^1$ is preferably a hydrocarbon group having 1 to 20 carbon atoms or a silicon containing group.

Examples of hydrocarbon group having 1 to 20 carbon atoms include alkyl groups such as methyl group, ethyl group, propyl group, butyl group, hexyl group, cyclohexyl group and octyl group; alkenyl groups such as vinyl group, propenyl group, cyclohexenyl group; arylalkyl groups such as benzyl group, phenylethyl group, phenylpropyl group; aryl groups such as phenyl group, tolyl group, dimethylphenyl group, trimethylphenyl group, ethylphenyl group, propylphenyl group, biphenyl group, naphthyl group, methylnaphthyl group, anthracenyl group and phenanthnyl group.

Examples of halogen containing hydrocarbon groups having 1 to 20 carbon atoms include p-fluorophenyl group, 3,5-difluorophenyl group, 3,4,5-trifluorophenyl group, pentafluorophenyl group, 3,5-bis(trifluoromethyl)phenyl group, and fluorobutyl group. As silicon containing group, silicon containing groups having 1 to 20 carbon atoms are preferable. Examples of those include monohydrocarbon substituted silyl groups such as methyldihydrosilyl group, phenyldihydrosilyl group; dihydrocarbon substituted silyl groups such as dimethylhydrosilyl group, diphenylhydrosilyl group, trihydrocarbon substituted silyl group such as trimethylsilyl group, triethylsilyl group, tripropylsilyl group, dimethyl(t-butyl)silyl group, tricyclohexylsilyl group, triphenylsilyl group, dimethylphenylsilyl group, methyldiphenylsilyl group, tritolylsilyl group, trinaphthylsilyl group; hydrocarbon substituted silylether groups such as trimethylsilylether; silicon substituted alkyl groups such as trimethylsilylmethyl group, bis(trimethylsilyl)methyl group, phenyldimethylsilylethyl group; silicon substituted aryl groups such as trimethylsilylphenyl group. Among them, silicon substituted alkyl groups are preferable, particularly trimethylsilylmethyl group and phenyldimethylsilylethyl group are preferred.

Examples of hetero-atom containing groups include methoxyethyl group, diisopropylaminoethyl group, furyl group, methyl furyl group, benzofuryl group, methylthioethyl group and thienyl group.

A represents a cross-linked group, and the atom bonding two indenyl rings is preferably an element in the group 14 of the periodic table. If there are two A or more, they may be the same or different with each other.

The element in the group 14 of the periodic table is preferably carbon, silicon, germanium or tin. Example of the group containing an element in the group 14 of the periodic table is represented by the general formula below

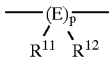

(wherein E represents carbon, silicon, tin or germanium; each of $R^{11}$ and $R^{12}$ represents respectively hydrogen atom, a hydrocarbon group having 1 to 20 carbon atoms, an alkoxy group having 1 to 20 carbon atoms, an aryloxy group having 6 to 20 carbon atoms or a silicon containing group having 1 to 20 carbon atoms, which may be the same or different with each other, or may form a ring by bonding with each other.)

Examples of hydrocarbon group having 1 to 20 carbon atoms and silicon containing group having 1 to 20 carbon atoms in above $R^{11}$ and $R^{12}$ include the same groups as described in above explanation of $R^1$ to $R^9$. Examples of alkoxy group having 1 to 20 carbon atoms and aryloxy group having 6 to 20 carbon atoms include methoxy group, ethoxy group, various propoxy groups, various butoxy groups, various pentoxy groups, various hexoxy groups, various octoxy groups, phenoxy group, methylphenoxy group and naphthoxy group.

Preferable example of A include $R^{10}{}_2C$ and $R^{10}{}_2Si$ (where $R^{10}$ represents hydrogen atom or a hydrocarbon group having 1 to 20 carbon atoms). p is an integer of 1 to 20, example of $(A)_p$ include methylene, ethylene, ethylidene, (tetramethyl)ethylene, isopropylidene, cyclohexylidene, 1,2-cyclohexylene, dimethylsilylene, diphenylsilylene, tetramethyldisilylene, dimethylgermylene, dimethylstanylene, 1,2-phenylene, vinylene, vinilydene, ethenylidene ($CH_2=C=$), among which methylene ($CH_2$), isopropylidene [$(CH_3)_2C$], ethylene ($CH_2CH_2$), (tetramethyl)ethylene [$(CH_3)_2C(CH_3)_2C$], dimethylsilylene [$(CH_3)_2Si$], diphenylsilylene [$(C_6H_5)_2Si$] are preferable in view of easiness of synthesis and high catalyst yield.

X represents a σ bonding ligand bonded to M, if X is plural, X may be the same or different. Examples of X include a halogen atom, a hydrocarbon group having 1 to 20 carbon atoms, an alkoxy group having 1 to 20 carbon atoms, an aryloxy group having 6 to 20 carbon atoms, an amide group having 1 to 20 carbon atoms, a silicon containing group having 1 to 20 carbon atoms, a phosphide group having 1 to 20 carbon atoms, a sulfide group having 1 to 20 carbon atoms, a sulfoxide group having 1 to 20 carbon atoms or an acyl group having 1 to 20 carbon atoms. Examples of halogen atoms include chlorine atom, fluorine atom, bromine atom or iodine atom. Examples of hydrocarbon group having 1 to 20 carbon atoms include alkyl groups such as methyl group, ethyl group, propyl group, butyl group, hexyl group, cyclohexyl group and octyl group; alkenyl groups such as vinyl group, propenyl group, cyclohexenyl group; arylalkyl groups such as benzyl group, phenylethyl group, phenylpropyl group; aryl groups such as phenyl group, tolyl group, dimethylphenyl group, trimethylphenyl group, ethylphenyl group, propylphenyl group, biphenyl group, naphthyl group, methylnaphthyl group, anthracenyl group and phenanthnyl group. Examples of alkoxy group having 1 to 20 carbon atoms include alkoxy groups such as methoxy group, ethoxy group, propoxy group, butoxy group; phenylmethoxy group, phenylethoxy group. Examples of aryloxy group include phenoxy group, methylphenoxy group, dimethylphenoxy group. Example of amide group having 1 to 20 carbon atoms include alkylamide groups such as dimethylamide group, diethylamide group, dipropylamide group, dibutylamide group, dicyclohexyl amide group, methylethylamide group; alkenylamide groups such as divinylamide group, dipropenyl amide group, dicyclohexnylamide group; arylalkylamide groups such as dibenzylamide group, phenylethylamide group, phenylpropylamide group; arylamide groups such as diphenylamide group, dinaphthylamide group. Examples of silicon containing groups having 1 to 20 carbon atoms include monohydrocarbon substituted silyl groups such as methyldihydrosilyl group, phenyldihydrosilyl group; dihydrocarbon substituted silyl groups such as dimethylhydrosilyl group, diphenylhydrosilyl group; trihydrocarbon substituted silyl groups such as trimethylsilyl group, triethylsilyl group, tripropylsilyl group, dimethyl(t-butyl)silyl group, tricyclohexylsilyl group, triphenylsilyl group, dimethylphenylsilyl group, methyldiphenylsilyl group, tritolylsilyl group, trinaphthylsilyl group; hydrocarbon substituted silyl ether groups such as trimethylsilylether; silicon substituted alkyl groups such as trimethylsilylmethyl group; silicon substituted aryl groups such as trimethylsilylphenyl group. Examples of sulfide group having 1 to 20 carbon atoms include alkylsulfide groups such as methylsulfide group, ethylsulfide group, propylsulfide group, butylsulfide group, hexylsulfide group, cyclohexylsulfide group, octylsulfide group; alkenylsulfide groups such as vinylsulfide group, propenylsulfide group, cyclohexenyl group; arylalkylsulfide groups such as benzylsulfide group, phenylethylsulfide group, phenylpropylsulfide group; arylsulfide groups such as phenylsulfide group, tolylsulfide group, dimethylphenylsulfide group, trimethylphenylsulfide group, ethylphenylsulfide group, propylphenylsulfide group, biphenylsulfide group, naphthylsulfide group, methylnaphthylsulfide group, anthoracenyl sulfide group, phenanthonylsulfide group. Examples of sulfoxide groups having 1 to 20 carbon atoms include alkylsulfoxide groups such as methylsulfoxide group, ethylsulfoxide group, propylsulfoxide group, butylsulfoxide group, hexylsulfoxide group, cyclohexylsulfoxide group, octylsulfoxide group; alkenylsulfoxide groups such as vinylsulfoxide group, propenylsulfoxide group, cyclohexenylsulfoxide group; arylalkylsulfoxide groups such as benzylsulfoxide group, phenylethylsulfoxide, phenylpropylsulfoxide group; arylsulfoxide groups such as phenylsulfoxide group, tolylsulfoxide group, dimethylphenylsulfoxide group, trimethylphenylsulfoxide group, ethylphenylsulfoxide group, propylphenylsulfoxide group, biphenylsulfoxide group, naphthylsulfoxide group, methylnaphthylsulfoxide group, anthracenylsulfoxide group, phenanthonylsulfoxide group. Examples of acyl group having 1 to 20 carbon atoms include alkylacyl groups such as formyl group, acetyl group, propionyl group, butylyl group, varelyl group, palmitoyl group, stearoyl group, oleoyl group; arylacyl groups such as benzoyl group, toloyl group, salicyloyl group, cinnamoyle group, naphthoyl group, phthaloyl group; oxalyl group, malonyl group succinyl group delivered respectively from dicarboxylic acids of oxalic acid, malonic acid, succinic acid. X is preferably alkyl groups such as methyl group, ethyl group and propyl group; aryl group such as phenyl group or halogen atoms such as chlorine atom.

Y represents Lewis base, and if Y is plural, they may be the same or different and may be cross-linked with other Y or cyclopentadienyl group or X. Example of Y include amines, ethers, esters, phosphines, thioethers, nitriles. Amines are amines having 1 to 20 carbon atoms, specifically, alkylamines such as methylamine, ethylamine, propylamine, butylamine, cyclohexylamine, methylethylamine, dimethylamine, diethylamine, dipropylamine, dibutylamine, dicyclohexylamine, methylethylamine, trimethylamine, triethylamine, tri-n-butylamine; alkenyl amines such as vinylamine, propenylamine, cyclohexenyl amine, divinylamine, dipropenyl amine, dicyclohexenylamine; arylalkylamines such as phenylmethylamine, phenylethylamine, phenylpropylamine; arylamines such as diphenylamine, dinaphthylamine; or ammonia, aniline, N-methylaniline, diphenylamine, N,N-dimethylaniline, methyldiphenylamine, pyridine, p-bromo-N,N-dimethylamine. Examples of ethers include aliphatic monoether compounds such as methylether, ethylether, propylether, isopropylether, butyl ether, isobutylether, n-amylether, isoamylether; multi-aliphatic ether compounds such as methylethylether, methylpropylether, methylisopropylether, methyl-n-amylether, methylisoamylether, ethylpropylether, ethylisopropylether, ethylbutylether, ethylisobutylether, ethyl-n-amylether, ethylisoamylether; unsaturated aliphatic ether compounds such as vinylether, allylether, methylvinylether, methylallylether, ethylvinylether, ethylallylether; aromatic ether compounds such as anisole, phenetole, phenylether, benzylether, phenylbenzylether, α-naphthyl ether, β-naphthylether; ring ether compounds such as ethylene oxide, propylene oxide, trimethylene oxide, tetrahydrofuran, tetrahydropyrane, dioxane. Examples of ester include ethylbenzoate. Examples of phosphines include phosphine having 1 to 20 carbon atoms, specifically, mono-hydrocarbon substituted phosphines such as methylphosphine, ethylphosphine, propylphosphine, butylphosphine, hexylphosphine, cyclohexylphosphine, octylphosphine; di-hydrocarbon substituted phosphines such as dimethylphosphine, diethylphosphine, dipropylphosphine, dibutylphosphine, dihexylphosphine, dicyclohexylphosphine, dioctylphosphine; tri-hydrocarbon substituted phosphines such as trimethylphosphine, triethylphosphine, tripropylphosphine, tributylphosphine, trihexylphosphine, tricyclohexylphosphine, trioctylphosphine; mono-alkenylphosphines such as vinylphosphine, propenylphosphine, cyclohexenylphosphine and dialkenylphosphines where hydrogen atom of phosphine is substituted by two alkenyl groups; trialkenylphosphines where hydrogen atom of phosphine is substituted by three alkenyl groups; arylalkylphosphines such as benzylphosphine, phenylethylphosphine, phenylpropylphosphine; arylphosphines such as diarylalkylphosphines or aryldialkylphosphines where hydrogen atom of phosphine is substituted by three aryl or alkenyl groups; phenylphosphine, trylphosphine, dimethylphenylphosphine, trimethylphenylphosphine, ethylphenylphosphine, propylphenylphosphine, biphenylphosphine, naphthylphosphine, methylnaphthylphosphine, anthracenylphosphine, phenanthnylphosphine; di(alkylaryl) phosphines where hydrogen atom of phosphine is substituted by two alkylaryl groups; tri(alkylaryl)phosphhines where hydrogen atom of phosphine is substituted by three alkylaryl groups. Examples of thioethers include above described sulfides. Examples of nitriles include acetonitrile and benzonitrile. q is an integer of 1 to 5 and represents [(valnce of M)−2], r is an integer of 0 to 3.

M represents a metal element in the groups 3 to 10 of the periodic table or in the lanthanide series, specifically, titanium, zirconium, hafnium, yttrium, vanadium, chrome, manganese, nickel, cobalt, palladium and lanthanide based metals, of which titanium, zirconium and hafnium in the group 4 elements are preferable for olefin polymerization catalyst.

Examples of those transition metal compounds include (1,2'-dimethylsilylene) (2,1'-dimethylsilylene)(indenyl)(3-trimethylsilylmethylindenyl)zirconiumdichloride, (1,2'-dimethylsilylene)(2,1'-dimethylsilylene)(indenyl)(3-methylindenyl) zirconiumdichloride, (1,2'-dimethylsilylene) (2,1'-dimethylsilylene) (indenyl)(3-trimethylsilylindenyl) ziconiumdichloride, (1,2'-dimethylsilylene)(2,1'-dimethylsilylene)(indenyl) (3-phenylindenyl) zirconiumdichloride, (1,2'-dimethylsilylene)(2,1'-dimethylsilylene)(indenyl)(3-benzylindenyl) zirconiumdichloride, (1,2'-dimethylsilylene) (2,1'-dimethylsilylene)(indenyl)(3-phenetylindenyl) zirconiumdichloride, (1,2'-ethylene)(2,1'-ethylene)(indenyl) (3-trimethylsilylmethylindenyl) zirconiumdichloride, (1,2'-ethylene)(2,1'-ethylene)(indenyl)(3-methylindenyl) zirconiumdichloride, (1,2'-ethylene)(2,1'-ethylene)(indenyl) (3-trimethylsilylindenyl) zirconiumdichloride, (1,2'-ethylene)(2,1'-ethylene)(indenyl)(3-phenylindenyl) zirconiumdichloride, (1,2'-ethylene)(2,1'-ethylene)(indenyl) (3-benzylindenyl) zirconiumdichloride, (1,2'-ethylene)(2,1'-ethylene)(indenyl)(3-neopentylindenyl) zirconiumdichloride, (1,2'-ethylene)(2,1'-ethylene)(indenyl) (3-phenetylindenyl) zirconiumdichloride, and those in which zirconium is replaced with titanium or hafnium, but they are not limited to those examples. Furthermore, they may be those compounds similar to above in which zirconium is replaced with a transition metal of other groups, or those compounds similar to above in which zirconium is replaced with a metal element of the lanthanide series.

Those transition metal compounds can be synthesized according to the method similar to that described in Journal of Organo-metallic Chemistry (J. Organomet. Chem.) Vol.369, p.359 (1989), namely, synthesis by reaction of the corresponding substituted cycloalkenyl anion with halide of above M is preferred.

The olefin polymerization catalyst of the present invention comprises (A) a transition metal compound represented by the above mentioned general formula (I) and an activating co-catalyst as the main components, this activating co-catalyst (B) is a compound which is capable of forming an ionic complex by reaction with the transition metal compound of above (A) component or its derivatives, or clay, mineral clay, or ion-exchange type compound, and (C) an organic aluminum compound to be used if necessary.

Preferable examples of the compound in above (B) component which is capable of forming an ionic complex by reaction with (A) component transition metal compound or its derivative include: (B-1) ionic compound which forms ionic complex by reaction with transition metal compound of (A) component, (B-2) aluminoxane or (B-3) Lewis acid, in view of high polymerization activity and low cost of catalyst.

Although any compound may be used as above (B-1) as long as it is an ionic compound capable of forming an ionic complex by reaction with above transition metal compound of (A) component, in view of an efficient formation of active sites, the compound represented by the general formulae (II) and (III) are preferable:

$$([L^1-R^{13}]^{h+})_a ([Z]^-)_b \quad (II)$$

$$([L^2]^{h+})_a ([Z]^-)_b \quad (III)$$

(where, $L^2$ is $M^1$, $R^{14}R^{15}M^2$, $R^{16}{}_3C$ or $R^{17}M^2$)

[In the formulae (II), (III), $L^1$ is a Lewis base, $[Z]^-$ is a non-coordinating anion $[Z^1]^-$ or $[Z^2]^-$, where $[Z^1]^-$ is an anion with plural groups bonded to an element, namely, $[M^3 G^1 G^2 \ldots G^f]$ (wherein $M^3$ is an element in the groups 5 to 15 of the periodic table, preferably in the groups 13 to 15 of the periodic table. Each of $G^1$ to $G^f$ respectively represents hydrogen atom, a halogen atom, an alkyl group having 1 to 20 carbon atoms, a dialkylamino group having 2 to 40 carbon atoms, an alkoxy group having 1 to 20 carbon atoms, an aryl group having 6 to 20 carbon atoms, an aryloxy group having 6 to 20 carbon atoms, an alkylaryl group having 7 to 40 carbon atoms, an arylalkyl group having 7 to 40 carbon atoms, a halogen substituted hydrocarbon group having 1 to 20 carbon atoms, an acyloxy group having 1 to 20 carbon atoms, an organic metalloid group or hetero-atom containing hydrocarbon group having 1 to 20 carbon atoms. Two or more of $G^1$ to $G^f$ may form a ring. f is an integer representing [(valence of center metal $M^3$)+1].), $[Z^2]^-$ represents Brønsted acid alone or a conjugate base in combination of Brønsted acid and Lewis acid, or a conjugate base generally defined as super acid, of which a logarithm of reciprocal of acid dissociation constant (pKa) is −10 or less. Or Lewis base may be coordinated. $R^{13}$ represents hydrogen atom, an alkyl group having 1 to 20 carbon atoms, an aryl group having 6 to 20 carbon atoms, an alkylaryl group or an arylalkyl group, each of $R^{14}$ and $R^{15}$ independently represents a cyclopentadienyl group, a substituted cyclopentadienyl group, an indenyl group, a substituted indenyl group, a fluorenyl group or a substituted fluorenyl group, $R^{16}$ represents an alkyl group having 1 to 20 carbon atoms, an aryl group, an alkylaryl group or an arylalkyl group. $R^{17}$ represents a large ring ligands such as tetraphenyl-porphyrin and phthalocyanine. h is an integer of 1 to 3 and represents ionic valence of $[L^1-R^{13}]$, $[L^2]$, a is an integer of 1 and larger, b=(h×a ). $M^1$ includes element of the groups 1 to 3, groups 11 to 13 and group 17 of the periodic table, $M^2$ represents an element of the groups 7 to 12 of the periodic table.].

Examples of $L^1$ include amines such as ammonia, methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline; phosphines such as triethylphosphine, triphenylphosphine, diphenylphosphine; thioethers such as tetrahydrothiophene; esters such as ethylbenzoate; nitriles such as acetonitrile and benzonitrile.

Examples of $R^{13}$ include hydrogen, methyl group, ethyl group, benzyl group and trityl group, examples of $R^{14}$, $R^{15}$ include cyclopentadienyl group, methyl cyclopentadienyl group, ethylcyclopentadienyl group and pentamethylcyclopentadienyl group. Examples of $R^{16}$ include phenyl group, p-tolyl group and p-methoxyphenyl group, examples of $R^{17}$ include tetraphenylporphine, phthalocyanine, allyl and methallyl. Examples of $M^1$ include Li, Na, K, Ag, Cu, Br, I, $I_3$, examples of $M^2$ include Mn, Fe, Co, Ni and Zn.

In $[Z^1]^-$, namely $[M^3\ G^1\ G^2\ \ldots\ G^f]$, examples of $M^3$ include B, Al, Si, P, As, Sb, of which B or Al is preferable. Examples of $G^1$, $G^2$ to $G^f$ include dialkylamino groups such as dimethylamino group, diethylamino group; alkoxy group or aryloxy group such as methoxy group and ethoxy group, n-butoxy group and phenoxy group; hydrocarbon groups such as methyl group, ethyl group, n-propyl group, isopropyl group, n-butyl group, isobutyl group, n-octyl group, n-eicosyl group, phenyl group, p-tolyl group, benzyl group, 4-t-butylphenyl group and 3,5-dimethylphenyl group; halogen groups such as fluorine, chlorine, bromine and iodine; heteroatom containing hydrocarbon groups such as p-fluorophenyl group, 3,5-difluorophenyl group, pentachlorophenyl group, 3,4,5-trifluorophenyl group, pentafluorophenyl group, 3,5-bis(trifluoromethyl) phenyl group and bis(trimethyl silyl)methyl group; organic metaloid groups such as pentamethylantimony group, trimethylsilyl group, trimethylgermyl group, diphenylarsine group, dicyclohexylantimony group and diphenylboron.

Examples of Brønsted acid alone or conjugate base in combination of Brønsted acid and Lewis acid $[Z^{2-}]^-$ with non-conjugate anion, namely, pKa of −10 and less include trifluoromethanesulfonate anion $(CF_3SO_3)^-$, bis(trifluoro methanesulfonyl)methyl anion, bis (trifluoromethanesulfonyl)benzyl anion, bis (trifluoromethanesulfonyl)amide, perchloric anion $(ClO_4)^-$, trifluoroacetic anion $(CF_3CO_2)^-$, hexafluoroantimon anion $(SbF_6)^-$, fluorosulfonic anion $(FSO_3)^-$, chlorosulfonic anion $(ClSO_3)^-$, fluorosulfonic anion/5-fluoroantimony $(FSO_3/SbF_5)^-$, fluorosulfonic anion/5-fluoroarsenic $(FS_3/AsF_5)^-$, trifluoromethane-sulfonic acid/5-fluoroantimony $(CF_3SO_3/SbF_5)^-$.

Examples of the ionic compounds which form ionic complex by reacting with transition metal of above (A) component, namely, (B-1) component compounds include triethylammonium tetraphenyl borate, tri-n-butylammonium tetraphenyl borate, trimethylammonium tetraphenyl borate, tetraethylammonium tetraphenyl borate, methyl(tri-n-butyl) ammonium tetraphenyl borate, benzyl(tri-n-butyl) ammonium tetraphenyl borate, dimethyldiphenylammonium tetraphenyl borate, triphenyl(methyl)ammonium tetraphenyl borate, trimethylanilinium tetraphenyl borate, methylpyridinium tetraphenyl borate, benzylpyridinium tetraphenyl borate, methyl(2-cyanopyridinium) tetraphenyl borate, triethylammonium tetrakis(pentafluorophenyl) borate, tri-n-butylammonium tetrakis(pentafluorophenyl) borate, triphenylammonium tetrakis(pentafluorophenyl) borate, tetra-n-butylammonium tetrakis(pentafluorophenyl) borate, tetraethylammonium tetrakis(pentafluorophenyl) borate, benzyl(tri-n-butyl)ammonium tetrakis (pentafluorophenyl) borate, methyldiphenyl ammonium tetrakis(pentafluorophenyl) borate, triphenyl(methyl) ammonium tetrakis(pentafluorophenyl) borate, methylanilinium tetrakis(pentafluorophenyl) borate, dimethylanilinium tetrakis-(pentafluorophenyl) borate, trimethylanilinium tetrakis(pentafluorophenyl) borate, methylpyridinium tetrakis(pentafluorophenyl) borate, benzylpyridinium tetrakis(pentafluorophenyl) borate, methyl(2-cyanopyridinium) tetrakis(pentafluorophenyl) borate, benzyl(2-cyanopyridinium) tetrakis(pentafluorophenyl) borate, methyl(4-cyanopyridinium) tetrakis (pentafluorophenyl) borate, triphenylphosphonium tetrakis (pentafluorophenyl) borate, dimethylanilinium tetrakis[3,5-di(trifluoromethyl)phenyl] borate, ferrocenium tetraphenyl borate, silver tetraphenyl borate, trityl tetraphenylborate, tetraphenylporphyrin manganese tetraphenyl borate, ferrocenium tetrakis(pentafluorophenyl) borate, (1,1'-dimethylferrocenium) tetrakis(pentafluorophenyl) borate, decamethylferrocenium tetrakis(pentafluorophenyl) borate, silver tetrakis(pentafluorophenyl) borate, trityl tetrakis (pentafluorophenyl) borate, lithium tetrakis (pentafluorophenyl) borate, sodium tetrakis (pentafluorophenyl) borate, tetraphenylporphyrin manganese tetrakis(pentafluorophenyl) borate, silver tetrafluoro borate, silver hexafluoro phosphate, silver hexafluoro arsenate, silver perchlorate, silver trifluoro acetate, silver trifluoromethane sulfate.

This (B-1) component, capable of forming an ionic complex by reacting with transition metal compound of (A) component, may be used alone, or in combination of more than two kinds.

On the other hand, examples of (B-2) component, aluminoxane, include chain aluminoxane represented by the general formula (IV) below, and ring aluminoxane represented by the general formula (V) below.

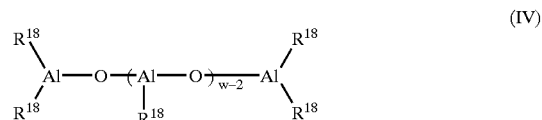

(IV)

(V)

(wherein, $R^{18}$ respectively represents alkyl group having 1–20 carbons, preferably having 1 to 8 carbons, and they may be the same or different. w is an integer of $2 \leq w \leq 40$, s is an integer of $1 < s \leq 50$).

Examples of above aluminoxanes include methylaluminoxane, ethylaluminoxane and isobutylaluminoxane.

One of the production method of above aluminoxanes is to bring alkyl-aluminum into contact with a condensing agent like water, but the method is not particularly limited, and the known methods may be employed. For instance, a method of bringing an organic aluminum, dissolved in an organic solvent, into contact with water; a method of adding an organic aluminum in the initial stage of polymerization, followed by adding water; a method of reacting water of crystallization contained in metal salts, or adsorbed water in inorganic or organic substances, with organic aluminum compound; a method of reacting tetra-alkyl dialuminoxane with trialkylaluminum, followed by reaction with water. Alumino-oxanes may be toluene-insoluble.

These aluminoxane may be used alone, or in combination of more than two kinds.

Lewis acid of (B-3) component is not particularly limited, and may be an organic compound or solid inorganic compound. Organic compounds such as boron compound and aluminum compound, inorganic compounds such as magnesium and aluminum compounds are preferably used because of an efficient formation of active sites. Examples of the aluminum compounds include bis(2,6-di-t-butyl-4-methylphenoxy)aluminum methyl, (1,1-bis-2-naphtoxy)-aluminum methyl, examples of magnesium compounds include magnesium chloride, diethoxy magnesium, examples of aluminum compounds include aluminum oxide, aluminum chloride, examples of boron compounds include triphenyl borane, tris(pentafluorophenyl) borane, tris[3,5-bis (trifluoromethyl) phenyl] borane, tris[(4-fluoromethyl) phenyl] borane, trimethyl borane, triethyl borane, tri-n-butyl borane, tris(fluoromethyl) borane, tris(pentafluoroethyl) borane, tris(nona fluorobutyl) borane, tris(2,4,6-trifluorophenyl) borane, tris(3,5-difluorophenyl) borane, tris [3,5-bis(trifluorophenyl)] borane, bis(pentafluorophenyl) fluoro borane, diphenylfluoro borane, bis (pentafluorophenyl)chloro borane, dimethylfluoro borane, diethylfluoro borane, di-n-butylfluoro borane, pentafluorophenyldichloro borane, methyldifluoro borane, ethyldifluoro borane and n-butyldifluoro borane.

These Lewis acids can be used alone, or in combination of two or more kinds.

On the other hand, in (B-4) clay, clay mineral or ion exchange compound in (B) component, clay is an agglomerate of fine silicatehydrate, and it is a material which becomes plastic with a suitable amount of water, becomes rigid when it is dried, and sinters when it is calcinated at high temperature. Clay mineral is a silicate hydrate, a main component of clay. Either clay or clay mineral may be used for preparation of above olefin polymerization catalyst component, and they may be natural or synthesized.

Ion exchanging stratified compound is a compound having a crystal structure of parallel stacked layers of surfaces formed by ionic bonding, bonded with each other by a weak bonding force, in which ions are exchangeable. Some clay minerals are ion exchanging stratified compound.

Examples of this (B-4) component include phyllosilicic acids as clay minerals. Phiyllosilicic acids include phyllosilicic acid and phyllosilicate. Examples of phyllosilicate as natural substances include smectites such as montmorillonite, saponite, hectolite; mica groups such as illite, sericite, and the mixed layer minerals of smectite group and mica group, or mica group and vermiculite group. Examples of synthesized substance include tetrasilicon fluoride mica, laponite, smecton. Non-clay mineral ionic crystal compounds having stratified crystal structure such as α-Zr $(HPO_4)_2$, γ-Zr $(HPO_4)_2$, α-Ti $(HPO_4)_2$, and γ-Ti $(HPO_4)_2$ can also be used.

Examples of the clay and clay minerals which does not belong to the ion exchanging stratified compound include clay which is called bentonite because of a low content of montmorillonite, Kibushi clay in which montmorillonite contains high amount of other components, gairome clay, sepiolite, polygorskite, and non-crystalline or low crystalline allophane, imogolite.

Furthermore, (B-4) component is preferably fine particles having volumetric average particle diameter of 10 μm or less, more preferably 3 μm or less. Fine particles generally has a particle size distribution. Volume average particle diameter of (B-4) component is preferably 10 μm or less, and the particle size distribution is such that the fraction of the particles of volume average particle diameter of 3 μm or less is 10 weight % or more, more preferable particle size distribution is such that the volume average particle diameter of 10 μm or less and the fraction having volume average particle diameter of 1.5 μm or less is 10 weight % or more. The measurement methods of volume average particle diameter and the content of fractions is, for example, by measuring laser light transmittance using an equipment (CIS-1 manufactured by GALAI Production Ltd.). (B-4) component may be the component treated with acid, alkali, salt or organic compound. Especially those pretreated with organic silicon compound or organic aluminum compound is preferable because of enhanced polymerization activity.

Among above (B-4) components, those highly capable of adsorbing quaternary ammonium salt (although not particularly limited, such as quaternary alkyl ammonium salt, quaternary aryl ammonium salt, quaternary arylalkyl ammonium salt, quaternary benzyl ammonium salt, heteroaromatic ammonium salt) or reacting with clay to form interlayer compound (intercalation) are preferable. For example, clay or clay minerals are preferable, specifically phyllosilicate is preferable, smectite is more preferable, and montmorillonite is particularly preferable. As synthesized substance, tetrasilicon fluoride mica is preferable.

In the polymerization catalyst of the present invention, the ratio of (A) catalyst component and (B) catalyst component, when (B-1) compound is used as (B) catalyst component, is preferably in the range of 10:1 to 1:100 in terms of molar ratio, more preferably in the range of 2:1 to 1:10, deviation from above range would cause catalyst cost high per unit weight polymer, and the catalyst would not be practically applicable. When (B-2) compound is used, above ratio in terms of molar ratio is preferably in the range of 1:1 to 1:1,000,000, more preferably in the range of 1:10 to 1:10,000. Deviation from above range, would cause catalyst cost high per unit weight of polymer, and the catalyst would not be practically applicable. The ratio of above (A) catalyst component and (B-3) catalyst component is preferably 10:1 to 1:2,000 in terms of molar ratio, more preferably 5:1 to 1:1,000, further more preferably in the range of 2:1 to 1:500, deviation from above range would cause catalyst cost high per unit weight of polymer, and the catalyst would not be practically applicable. The ratio of (A) component and (B-4) component is defined based on a unit weight [g] of (B-4) component such as clay, in the range of 0.1 to 1,000 micro mol, preferably 1 to 100 micro mol of transition metal complex of (A) component.

(B-1), (B-2), (B-3), (B-4) as catalyst component (B), may be used alone or in combination of two or more kinds.

Polymerization catalyst of the present invention may contain above (A) component and (B) component as the main components, or may contain (A) component, (B) component and (C) organic aluminum compound as the main components.

As (C) component, organic aluminum compound represented by the general formula (VI) is used:

$$R^{19}{}_v Al\ Q_{3-v} \qquad\qquad (VI)$$

(wherein, $R^{19}$ represents an alkyl group having 1 to 10 carbon atoms, Q represents hydrogen atom, an alkoxyl group having 1 to 20 carbon atoms, or a halogen atom, v is an integer of 1 to 3).

Examples of the compound represented by above general formula (VI) include trimethylaluminum, triethylaluminum, triisopropylaluminum, triisobutyl aluminum, dimethylaluminum chloride, diethylaluminum chloride, methylaluminum dichloride, ethylaluminum dichloride, dimethylaluminum fluoride, diisobutylaluminum hydride, diethylaluminum hydride, ethylaluminum sesqui chloride. Among those organic aluminum compound, trialkylaluminum is preferable, particularly trimethylaluminum and triisobutylaluminum are suitable.

Those organic aluminum may be used alone or in combination of two or more kinds.

The ratio of above (A) catalyst component and (C) catalyst component for use is preferably in the range of 1:1 to 1:10,000, more preferably in the range of 1:5 to 1:2,000, further more preferably in the range of 1:10 to 1:1,000 in terms of molar ratio. By using the (C) catalyst component, polymerization activity per unit transition metal can be improved, but if it is excessive, particularly when deviating from above range, organic aluminum compound is wasted and remains in a large amount in the polymer, while if it is insufficient, sometimes enough catalyst activity is not obtained and therefore not preferable.

In the present invention, in contacting each component, or after contacting, polymers such as polyethylene, polypropylene, and inorganic oxide such as silica, alumina may coexist or brought into contact. For depositing on a carrier, it is preferable to deposit on a polymer, and for such carrier polymer, particle size is normally 1 to 300 μm, preferably 10 to 200 μm, more preferably 20 to 100 μm. If this particle size is smaller than 1 μm, fine powder increases in the polymer, if this particle size is 300 μm or more, coarse particles in the polymer increase, resulting in decrease of bulk density and plugging in a hopper at the production process. In this case, specific surface area of the carrier is 1 to 1,000 $m^2/g$, preferably 50 to 500 $m^2/g$, pore volume is 0.1 to 5 $m^3/g$, preferably 0.3 to 3 $m^3/g$.

Contact with each component may be conducted in an inert gas such as nitrogen, or in hydrocarbon such as pentane, hexane, heptane, toluene and xylene. Addition or contact of each component may be, of course, conducted at polymerization temperature, but also in the range of −30° C. to the boiling point of each solvent, particularly in the range of room temperature to the boiling point of the solvent is preferable.

The olefin based polymer of the present invention is the polymer obtained using above olefin polymerization catalyst, through homopolymerization of olefins or copolymerization of olefins with other olefins and/or other monomers, under the presence of the above mentioned olefin polymerization catalyst.

In the production method of the olefin polymer of the present invention, organic aluminum compound (C) may be brought into contact with (A) component and/or (B) component in advance, or placing (C) component in advance in a reactor, followed by contacting with (A) component and (B) component. The amount of (C) component to be used is the same as above catalyst for olefin polymerization. By employing the olefin polymerization method of the present invention, using above described polymerization catalyst, homopolymerization of olefins, or copolymerization of olefins and other olefins and/or other monomers (namely, copolymerization of different kinds of olefins with each other, copolymerization of olefins and other monomers, or copolymerization of different kinds of olefins with each other as well as with other monomers) can be suitably conducted.

Although there is no particular limitation to the olefins to be used, ethylene or α-olefin having 3 to 20 carbon atoms is preferable. Examples of the α-olefins include α-olefins such as propylene, 1-butene, 1-pentene, 1-hexene, 1-heptene, 1-octene, 1-nonene, 1-decene, 4-phenyl-1-butene, 6-phenyl-1-hexene, 3-methyl-1-butene, 4-methyl-1-butene, 3-methyl-1-pentene, 4-methyl-1-hexene, 5-methyl-1-hexene, 3,3-dimethyl-1-pentene, 3,4-dimethyl-1-pentene, 4,4-dimethyl-1-pentene, vinylcyclohexene; dienes such as 1,3-butadiene, 1,4-pentadiene, 1,5-hexadiene; halogen substituted α-olefins such as hexafluoropropene, tetrafluoro ethylene, 2-fluoropropene, fluoroethylene, 1,1-difluoroethylene, 3-fluoro propene, trifluoroethylene, 3,4-dichloro-1-butene; cyclic olefins such as cyclopentene, cyclohexene, norbornene, 5-methylnorbornene, 5-ethyl norbornene, 5-propylnorbornene, 5,6-dimethylnorbornene, 5-benzylnorbornene; as styrenes, alkylstyrenes such as styrene, p-methylstyrene, p-ethylstyrene, p-propylstyrene, p-isopropylstyrene, p-butylstyrene, p-tert-butylstyrene, p-phenylstyrene, o-methylstyrene, o-ethylstyrene, o-propylstyrene, o-isopropyl styrene, m-methylstyrene, m-ethylstyrene, m-isopropylstyrene, m-butylstyrene, mesitylstyrene, 2,4-dimethylstyrene, 2,5-dimethylstyrene, 3,5-dimethylstyrene; alkoxy styrenes such as p-methoxystyrene, o-methoxystyrene, m-methoxy styrene, halogenated styrenes such as p-chlorostyrene, m-chlorostyrene, o-chlorostyrene, p-bromostyrene, m-bromostyrene, o-bromostyrene, p-fluoro styrene, m-fluorostyrene, o-fluorostyrene, o-methyl-p-fluorostyrene, trimethylsilylstyrene, vinylbenzoate ester and divinylbenzene. Other olefins above described may be selected from above olefins.

In the present invention, above olefins may be used alone, or in combination of two kinds or more. When copolymerizing two kinds or more olefins, above olefins may be optionally combined.

Moreover, in the present invention, above olefins may be copolymerized with other monomers, and examples of the other monomers to be used include chain diolefins such as butadiene, isoprene, 1,4-pentadiene, 1,5-hexadiene; polycyclic olefins such as norbornene, 1,4,5,8-dimethano-1,2,3,4, 4a,5,8,8a-octahydro naphthalene, 2-norbornene; cyclic diolefins such as norbornadiene, 5-ethylidene norbornene, 5-vinylnorbornene, dicyclopentadiene; unsaturated esters such as ethylacrylate and methylmetacrylate.

In the present invention, olefin polymerization method is not particularly limited, and any method such as slurry polymerization method, solution polymerization method, gas phase polymerization method, bulk polymerization method and suspension polymerization method may be employed.

When using polymerization solvent, examples of the solvent include hydrocarbons and halogenated hydrocarbons such as benzene, toluene, xylene, n-hexane, n-heptane, cyclohexane, methylene chloride, chloroform, 1,2-dichloroethane and chlorobenzene. Those may be used alone, or in combination of two kinds or more. Monomer for polymerization can also be used as solvent depending on its kind.

Amount of catalyst to be used in polymerization, per 1 liter of solvent, is selected so that (A) component to be normally in the range of 0.5 to 100 micromol, preferably 2 to 25 micromol because of advantage in polymerization activity and reactor efficiency.

As for the polymerization conditions, pressure is normally selected in the range of atmospheric pressure to 200 MPa·G. Reaction temperature is normally in the range of −50° C. to 250° C. The methods of controlling molecular weight of the polymer include kind of catalyst, amount of catalyst used, selection of polymerization temperature and introduction of hydrogen.

Furthermore, in the olefin polymerization of the present invention, a preliminary polymerization can be conducted using above catalysts. This preliminary polymerization can be conducted by bringing catalyst into contact with a small amount of olefin, at reaction temperature of −20 to 100° C., preferably −10 to 70° C., and 0 to 50° C. is particularly preferable. Solvent to be used for this preliminary polymerization include inert hydrocarbons, aliphatic hydrocarbons, aromatic hydrocarbons and monomers, of which particularly aliphatic hydrocarbon is preferable. This preliminary polymerization can also be conducted without using solvent. The preliminary polymerization is preferably conducted so that the product polymer has an intrinsic viscosity [η] (measured in decalin at 135° C.) of 0.2 deciliter/g, preferably 0.5 deciliter/g or higher, and the condition is adjusted so that the amount of the preliminary polymerized polymer is 1 to 10,000 g, preferably, 10 to 1,000 g per 1 mmol of the transition metal in the catalyst. By this production method, particularly polypropylene, polyethylene or copolymers of propylene and ethylene and/or α-olefin having 4 to 20 carbon atoms is obtained with high molecular weight and high polymerization activity.

Specific examples of the olefin based polymer of the present invention include polypropylene, polyethylene, or copolymers of propylene and ethylene, and/or α-olefin having 4 to 20 carbon atoms.

Stereoregularity of the olefin based polymer is preferably 40 to 80%, more preferably 45 to 80% in terms of mesopentad fraction [mmmm] measured by $^{13}$C-NMR. If the mesopentad fraction [mmmm] is 40% or less, surface of the olefin based polymer may become sticky.

The olefin based polymer of the present invention has homogeneous composition and narrow molecular weight distribution. Molecular weight distribution (Mw/Mn) is normally 5 or less, preferably 4 or less.

In the following, the present invention is described in more detail by examples, however, the present invention is by no means limited by those examples.

EXAMPLE 1

Synthesis of (1,2'-SiMe$_2$)(2,1'-SiMe$_2$)(indenyl)(3-trimethylsilylmethylindenyl) zirconiumdichloride (1)

Under nitrogen gas flow, 50 ml of ether and 3.5 g (10.2 mmol) of (1,2'-SiMe$_2$)(2,1'-SiMe$_2$) bis(indene) were placed in a 200 ml Schlenk tube, into which hexane solution of n-butyllithium (n-BuLi) (1.60 mol/l, 12.8 ml) was dropped at −78° C. After stirring for 8 hours at room temperature, the solvent was distilled off, and the remaining solid was dried under a reduced pressure to obtain 5.0 g of white solid. This solid was dissolved in 50 ml of tetrahydrofuran (THF), into which 1.4 ml of iodomethyltrimethylsilane was dropped at room temperature. After hydrolysis with 10 ml of water, and extraction of organic phase with 50 ml of ether, it was dried under a reduced pressure. After 50 ml of ether was added to this, into which hexane solution of n-BuLi (1.6 mol/l, 12.4 ml) was dropped at −78° C., then the solution was heated to room temperature, followed by stirring for three hours, ether was distilled off. Obtained solid was washed with 30 ml of hexane and vacuum dried. 5.11 g of this white solid was suspended in 50 ml of toluene, into which 2.0 g of zirconiumtetrachloride (8.6 mmol) suspended in 10 ml of toluene, prepared in another Schlenk tube, was added. After stirring at room temperature for 12 hours, the solvent was distilled off and the residue was washed with 50 ml of hexane, then the residue was recrystallized to obtain 1.2 g of yellow fine crystals (yield 25%).

$^1$H-NMR (90 MHz, CDCl$_3$): δ−0.09 (s, —SiMe$_3$, 9H); 0.89, 0.86, 1.03, 1.06 (s, —Me$_2$Si—, 12H); 2.20, 2.65 (d, —CH$_2$—, 2H); 6.99 (s, CH, 1H); 7.0–7.8 (m, ArH, 8H)

EXAMPLE 2

Polymerization of Propylene

In a heat dried 1 liter autoclave, under nitrogen gas flow, 400 ml of toluene and 0.5 mmol of triisobutylaluminum were placed at room temperature. After heating up to 50° C. under stirring, 1 mmol of methylaluminoxane and 1 micromol of (1,2'-SiMe$_2$)(2,1'-SiMe$_2$)(indenyl)(3-trimethylsilylmethylindenyl) zirconiumdichloride obtained in Example 1 were added, and polymerization took place for one hour keeping the pressure at 0.7 MPa·G by propylene. After the polymerization was completed, the product was thrown into methanol and stirred well, filtered, washed enough with methanol and dried to obtain 38.8 g of polypropylene. Intrinsic viscosity of the obtained polymer was 2.71 dl/g, weight average molecular weight (Mw) was 521,000, weight average molecular weight/number average molecular weight ratio (Mw/Mn) was 2.95, mesopentad fraction [mmmm] was 46.4%, and the melting point was 80.4° C.

Mesopentad fraction [mmmm] was defined as the fraction of surface area, occupied by 21.8 ppm signal attributed to mesopentad, in the total area of 9 signals appearing 19.0 to 22.5 ppm of $^{13}$C-NMR of the polymer, and was measured by the following equipment and conditions:

Equipment: JEOL Ltd. JNM-EX400 type NMR equipment
Measuring nucleus: $^{13}$C (100.4 MHz)
Method: $^1$H complete de-coupling method
Concentration: about 200 mg/3 ml (6.7×10 kg/m$^3$) (10φ sampling tube)
Solvent: mixed solvent of 1,2,4-trichlorobenzene and benzene-d$_6$ in 90:10 (volume ratio).
Temperature: 130° C.
Pulse width: 45° C.
Pulse repeating time: 4 second
Summation: 1000 times Melting point was measured under the following conditions:

Equipment: DSC7 manufactured by Perkin Elmer Instruments LLC.
Heating rate: 10° C./min.
Temperature range: −50° C. to 150° C.

Intrinsic viscosity [η] was measured using Rigou Ltd. VMR-053 type automatic viscometer, at 135° C. in decalin.

Molecular weight and molecular weight distribution were measured by Gel Permeation Chromatography (GPC) method, converted to polyethylene equivalent using the following equipment and conditions:

Equipment: Waters ALC/GPC 150C
Column: manufactured by TOSOH Ltd. GMHHR +H(S) HT×2
Temperature: 145° C.
Solvent: 1,2,4-trichlorobenzene
Flow rate: 1 ml/min

EXAMPLE 3

Polymerization of Propylene

In a heat-dried 1 liter autoclave, under nitrogen gas flow, 400 ml of heptane and 0.2 mmol of triisobutylaluminum were placed at room temperature. After heating to 60° C. under stirring, 0.5 mmol of methylaluminoxane and 0.5 micromol of (1,2'-SiMe$_2$)(2,1'-SiMe$_2$)(indenyl)(3-trimethylsilylmethylindenyl) zirconium dichloride obtained in Example 1 were added, then introducing hydrogen of 0.03 MPa·G, polymerization took place for 30 minutes keeping the pressure at 0.8 MPa·G by propylene. After the polymerization was completed, the product was thrown into methanol and stirred well, filtered, washed enough with methanol and dried to obtain 32.6 g of polypropylene.

Melting point of the obtained polymer was 100.2° C., Mw was 39,460, Mw/Mn was 2.58 and mesopentad fraction [mmmm] was 59.3%.

EXAMPLE 4

Polymerization of Propylene

The polymerization was conducted in the same manner as Example 3, except that hydrogen was not introduced. 6.9 g of polypropylene was obtained. Intrinsic viscosity of the obtained polymer was 1.39 dl/g, Mw was 181,000, Mw/Mn was 2.72, mesopentad fraction [mmmm] was 53.2% and melting point was 90.8° C.

Polymerization in Example 2 was conducted at 50° C., while polymerization in Example 3 and 4 were conducted at 60° C. In comparison with Example 2, polymers in Example 3 and 4 have equivalent mesopentad fraction [mmmm] and melting point, indicating superiority of the polymerization catalyst of the present invention in thermal resistivity in view of stereoregularity and melting point.

Comparative Example 1

The polymerization was conducted in the same manner as in Example 2, except that (1,2'-SiMe$_2$)(2,1'-SiMe$_2$)(tetrahydroindenyl)$_2$ zirconiumdichloride was used instead of (1,2'-SiMe$_2$)(2,1'-SiMe$_2$)(indenyl)(3-trimethylsilylmethylindenyl) zirconiumdichloride. 15.6 g of isotactic polypropylene was obtained. Melting point of the obtained polymer was 116.0° C., Mw was 15,000, Mw/Mn was 1.7, mesopentad fraction [mmmm] was 75.7%.

In Example 2 and Comparative Example 1, polymerization of propylene was conducted under the same condition except that the kind of transition metal compound was different. However, although a high melting point was obtained in the Comparative Example 1, polymerization activity was low and weight average molecular weight was low in comparison with Example 2 wherein double cross-linked metallocene complex was used.

Comparative Example 2

In a heat-dried 1 liter autoclave, under nitrogen gas flow, 400 ml of toluene, 0.5 mmol of triisobutylaluminum (TIBA) and 1 mmol of methylaluminoxane were placed at room temperature. After heating to 50° C. under stirring, 1 micromol of (1,2'-SiMe$_2$)(2,1'-SiMe$_2$)-bis(3-ethoxymethylindenyl)zirconium dichloride was added, then polymerization took place for 1 hour keeping the pressure at 0.7 MPa·G by propylene. After the polymerization was completed, the product was thrown into methanol and stirred well, filtered, washed enough with methanol and dried to obtain 36.4 g of isotactic polypropylene.

Melting point of the obtained polymer was 72.2° C., intrisic viscosity of 3.33 dl/g, Mw was 455,000, Mw/Mn was 2.87, mesopentad fraction [mmmm] was 39.1%.

Comparative Example 3

In a heat-dried 1 liter autoclave, under nitrogen gas flow, 400 ml of toluene, 0.5 mmol of TIBA and 0.5 mmol of methylaluminoxane were placed at room temperature. After heating to 50° C. under stirring, 0.5 micromol of (1,2'-SiMe$_2$)(2,1'-SiMe$_2$)-bis(3-trimethylsilylmethylindenyl) zirconium dichloride was added, then polymerization took place for 1 hour keeping the pressure at 0.7 MPa·G by propylene. After the polymerization was completed, the product was thrown into methanol-hydrocloric acid solution and stirred well, filtered, washed enough with methanol and dried to obtain 70.1 g of isotactic polypropylene. Melting point of the obtained polymer was 73.5° C., intrisic viscosity of 3.39 dl/g, Mw was 478,000, Mw/Mn was 2.46, mesopentad fraction [mmmm] was 39.8%.

In Example 2 and Comparative Example 2 and 3, polymerization of propylene was conducted under almost the same condition except that the kind of transition metal was different. As the result, in comparison with Example 2, low melting point polymer was obtained in Comparative Example 2 and 3. Moreover, in comparison with Example 2, polymers obtained in Comparative Examples 2 and 3 have slightly lower weight average molecular weight, and mesopentad fraction [mmmm], as an index of stereoregularity, was also low.

Possibility of Industrial Application

Transition metal compound of the double cross-linked type metallocene complex of the present invention is highly efficient for production and useful as a component of olefin polymerization catalyst. The olefin polymerization catalyst containing the transition metal compound of the present invention is highly active, and efficiently provides olefin based homopolymer or copolymer having homogeneous composition, narrow molecular weight distribution, and high stereoregularity.

What is claimed is:

1. A transition metal compound represented by the general formula (I):

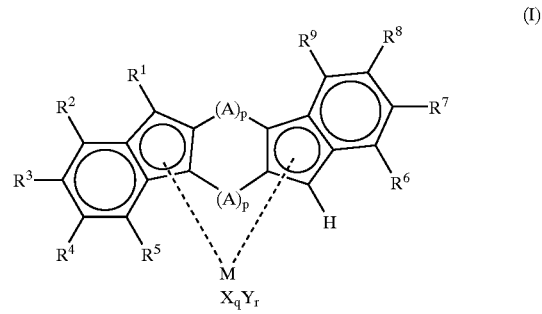

wherein M represents a metal element in the groups 3 to 10 of the periodic table or in the lanthanoid series;

X represents a σ bonding ligand bonded to m, if X is plural, X may be the same or different, or cross-linked with indenyl ring or Y;

Y represents a Lewis base, if Y is plural, Y may be the same or different, or may be cross-linked with indenyl ring or X;

A represents $R^{10}{}_2$ Si, wherein $R^{10}$ represents hydrogen atom or a hydrocarbon group having 1 to 20 carbons atoms;

p is an integer of 1 to 20;

q is an integer of 1 to 5 and represents {(valence of M)-2};

r is an integer of 0 to 3;

$R^1$ represents a halogen containing hydrocarbon group having 1 to 20 carbon atoms, a silicon containing group or a hetero-atom containing group;

each of $R^2$ to $R^9$ represents respectively hydrogen atom, a halogen atom, a hydrocarbon group having 1 to 20 carbon atoms, a halogen containing hydrocarbon group having 1 to 20 carbon atoms, a silicon containing group or a hetero-atom containing group, each of $R^2$ $R^9$ may be the same or different from each other, or may form a ring with a neighboring group.

2. The transition metal compound according to claim 1, in which (A)p in the general formula (I) is $(CH_3)_2$ Si or $(C_6H_5)_2$ Si.

3. The transition metal compound according to claim 1, in which $R^1$ in the general formula (I) is a silicon containing group.

4. The transition metal compound according to claim 1, in which M in the general formula (I) is a metal element of group 4 of the periodic table.

5. An olefin polymerization catalyst, comprising:
   (A) a transition metal compound as claimed in claim 1; and
   (B) an activating co-catalyst, as the main components.

6. The olefin polymerization catalyst according to claim 5, wherein the said activating co-catalyst (B) is a compound forming an ionic complex by reacting with the transition metal compound of the component (A) or its derivative, or clay, clay minerals or an ion exchanging stratified compound.

7. The olefin polymerization catalyst according to claim 5, wherein the said activating co-catalyst (B) is a combination of a compound forming an ionic complex by reacting with the transition metal compound of the component (A) or its derivative, or clay, clay minerals or an ion exchanging stratified compound, and (C) organic aluminum compound.

8. A polypropylene polymer obtained by using the olefin polymerization catalyst according to claim 5.

9. The polypropylene according to claim 8, wherein a mesopentad fraction as a stereoregularity index, measured by $^{13}$C-NMR, is 40 to 80%.

10. The polypropylene according to claim 8, having an intrinsic viscosity of 1.39 dl/g or more.

11. A polypropylene obtained by using the olefin polymerization catalyst according to claim 6.

12. The polypropylene according to claim 11, wherein a mesopentad fraction as a stereoregularity index, measured by $^{13}$C-NMR, is 40 to 80%.

13. The polypropylene according to claim 11, having an intrinsic viscosity of 1.39 dl/g or more.

14. An polypropylene obtained by using the olefin polymerization catalyst according to claim 7.

15. The polypropylene according to claim 14, wherein a mesopentad fraction as a stereoregularity index, measured by $^{13}$C-NMR, is 40 to 80%.

16. The polypropylene according to claim 14, having an intrinsic viscosity of 1.39 dl/g or more.

17. A method for producing a polypropylene, comprising:
   homopolymerizing propylene or copolymerizing a propylene with another olefin and/or other monomer in the presence of the olefin polymerization catalyst according to claim 5.

18. A method for producing a polypropylene, comprising:
   homopolymerizing propylene or copolymerizing a propylene with another olefin and/or other monomer in the presence of the olefin polymerization catalyst according to claim 6.

19. A method for producing a polypropylene comprising:
   homopolymerizing propylene or copolymerizing a propylene with another olefin and/or other monomer in the presence of the olefin polymerization catalyst according to claim 7.

* * * * *